(12) United States Patent
Yuasa

(10) Patent No.: US 10,578,485 B2
(45) Date of Patent: Mar. 3, 2020

(54) SPECTROSCOPIC INSTRUMENT

(71) Applicant: TOPCON Corporation, Tokyo-to (JP)

(72) Inventor: Taichi Yuasa, Tokyo-to (JP)

(73) Assignee: TOPCON Corporation, Tokyo-to (JP)

( * ) Notice: Subject to any disclaimer, the term of this patent is extended or adjusted under 35 U.S.C. 154(b) by 518 days.

(21) Appl. No.: 15/284,886

(22) Filed: Oct. 4, 2016

(65) Prior Publication Data
US 2017/0102265 A1 Apr. 13, 2017

(30) Foreign Application Priority Data

Oct. 7, 2015 (JP) .................................. 2015-199194

(51) Int. Cl.
| | |
|---|---|
| *G01J 3/00* | (2006.01) |
| *G01J 3/02* | (2006.01) |
| *G02B 27/00* | (2006.01) |
| *G02B 5/10* | (2006.01) |
| *G02B 13/18* | (2006.01) |
| *G01J 3/10* | (2006.01) |
| *G01J 3/42* | (2006.01) |
| *G01N 21/27* | (2006.01) |
| *G01N 33/38* | (2006.01) |

(52) U.S. Cl.
CPC .............. *G01J 3/0208* (2013.01); *G01J 3/108* (2013.01); *G01J 3/42* (2013.01); *G01N 21/27* (2013.01); *G02B 5/10* (2013.01); *G02B 13/18* (2013.01); *G02B 27/0025* (2013.01); *G01N 33/383* (2013.01); *G01N 2201/061* (2013.01); *G01N 2201/0638* (2013.01)

(58) Field of Classification Search
USPC ........................................................ 356/4.01
See application file for complete search history.

(56) References Cited

U.S. PATENT DOCUMENTS

| | | | |
|---|---|---|---|
| 4,756,619 A | 7/1988 | Gerlinger et al. | |
| 4,917,495 A | 4/1990 | Steenhoek | |
| 8,189,191 B2 * | 5/2012 | Webb ........................ | G01J 3/02 356/326 |
| 9,075,227 B2 * | 7/2015 | Rachet ................ | G02B 21/0032 |
| 2007/0201027 A1 * | 8/2007 | Doushkina ............. | G01N 21/47 356/338 |

(Continued)

FOREIGN PATENT DOCUMENTS

| | | |
|---|---|---|
| JP | 56-147034 A | 11/1981 |
| JP | 59-3330 A | 1/1984 |

(Continued)

*Primary Examiner* — James R Hulka
(74) *Attorney, Agent, or Firm* — Nields, Lemack & Frame, LLC

(57) ABSTRACT

The invention provides a spectroscopic instrument, which comprises a projecting optical system for projecting a projecting light emitted from a light source, a photodetecting optical system for receiving a reflection light from an object to be measured and for guiding to a photodetection member, and a spectroscope for detecting a condition of the object to be measured based on the reflection light as received by the photodetection member, wherein the projecting optical system and the photodetecting optical system have a projecting system chromatic aberration decreasing component and a photodetecting system chromatic aberration decreasing component which eliminate chromatic aberrations, respectively.

12 Claims, 2 Drawing Sheets

(56) References Cited

U.S. PATENT DOCUMENTS

| | | | |
|---|---|---|---|
| 2009/0091723 A1* | 4/2009 | Sasaki | B82Y 10/00 355/53 |
| 2009/0201499 A1* | 8/2009 | Monk | G01J 3/02 356/310 |
| 2011/0272096 A1* | 11/2011 | Serikawa | G01N 21/956 156/345.24 |
| 2011/0279887 A1* | 11/2011 | Li | G01J 3/18 359/333 |
| 2011/0300490 A1* | 12/2011 | Rachet | G02B 21/0032 430/322 |
| 2012/0120387 A1 | 5/2012 | Meloni et al. | |

FOREIGN PATENT DOCUMENTS

| | | |
|---|---|---|
| JP | 63-16247 A | 1/1988 |
| JP | 2-245623 A | 10/1990 |
| JP | 3-72228 A | 3/1991 |
| JP | 2000-14779 A | 1/2000 |
| JP | 2009-156809 A | 7/2009 |

\* cited by examiner

SPECTROSCOPIC INSTRUMENT

BACKGROUND OF THE INVENTION

The present invention relates to a spectroscopic instrument, which performs spectroscopy based on a reflection light from an object to be measured.

In building structures such as bridges, tunnels, and the like, a large amount of concrete is used on leg portions, wall surfaces, and the like. The concrete deteriorates over time due to salty substances in the atmosphere or the like. Therefore, as a purpose of maintenance operation, it is necessary to periodically measure the salinity concentration in the concrete and to judge the degree of deterioration of the concrete.

A spectroscopic instrument is known as an instrument for measuring the salinity concentration in the concrete on a non-contact basis. The spectroscopic instrument can measure the salinity concentration in the concrete by projecting a near-infrared light to the concrete and by analyzing the reflection light from the concrete, and the degree of deterioration of the concrete is judged based on the salinity concentration.

As a light source to be used by the spectroscopic instrument, a halogen lamp, a halogen heater, and the like can be given, for instance. In a case of the halogen lamp or the halogen heater, the light as emitted includes the near-infrared light with a wavelength of about 0.8 µm to 2.5 µm, and has stability with respect to temperature change and the like. Further, the halogen lamp or the halogen heater is suitable as the light source of the spectroscopic instrument since a measurable amount of light can be obtained even in a case where the distance from the light source to the object to be measured is about 10 meters.

In the spectroscopic measurement, it is necessary to obtain a high wavelength resolving power in order to improve measurement accuracy. However, in a case where there is chromatic aberration in an optical system, a focal length changes per each wavelength, and there is a possibility that a curve of spectral characteristics may change per each distance. Therefore, there is a possibility that the chromatic aberration may become a hindrance to the improvement of the measurement accuracy.

Further, conventionally, in order to correct an influence of chromatic aberration, a measurement is carried out per each distance regarding a predetermined reference diffusing reflecting object and stored as a reference value in advance, and the influence of the chromatic aberration is corrected by comparing the measurement results with the reference value corresponding to the distance to the object to be measured, when the measurement is carried out. Therefore, it took a lot of working time and working efficiency was low.

SUMMARY OF THE INVENTION

It is an object of the present invention to decrease a chromatic aberration of an optical system and to provide a spectroscopic instrument which improve measurement accuracy.

To attain the object as described above, a spectroscopic instrument according to the present invention comprises a projecting optical system for projecting a projecting light emitted from a light source, a photodetecting optical system for receiving a reflection light from an object to be measured and for guiding to a photodetection member, and a spectroscope for detecting a condition of the object to be measured based on the reflection light as received by the photodetection member, wherein the projecting optical system and the photodetecting optical system have a projecting system chromatic aberration decreasing component and a photodetecting system chromatic aberration decreasing component which eliminate chromatic aberrations, respectively.

Further, in the spectroscopic instrument according to the present invention, the photodetecting optical system has a mirror for reflecting one part of the reflection light from the object to be measured, wherein the projecting optical system and the photodetecting optical system are disposed in such a manner that a projecting optical axis and a photodetecting optical axis cross each other, and the mirror is provided at a crossing position of the projecting optical axis and the photodetecting optical axis.

Further, in the spectroscopic instrument according to the present invention, a diameter of the projecting system chromatic aberration decreasing component is larger than a diameter of the mirror.

Further, in the spectroscopic instrument according to the present invention, the projecting system chromatic aberration decreasing component is a projecting system lens group having a projecting system concave lens and a projecting system convex lens, and the photodetecting system chromatic aberration decreasing component is a photodetecting system lens group having a photodetecting system concave lens and a photodetecting system convex lens.

Further, in the spectroscopic instrument according to the present invention, the projecting system chromatic aberration decreasing component is a projecting system reflection mirror having a reflection surface of a free form surface or an off-axis paraboloid surface, and the photodetecting system chromatic aberration decreasing component is a photodetecting system reflection mirror having a reflection surface of a free form surface or an off-axis paraboloid surface.

Furthermore, in the spectroscopic instrument according to the present invention, the light source is a filament for emitting the projecting light including a near-infrared light, wherein the projecting optical system has an elliptical mirror, and the projecting system chromatic aberration decreasing component is disposed so that a focusing position of the projecting light reflected by the elliptical mirror approximately coincides with a focal position of the projecting system chromatic aberration decreasing component.

According to the present invention, the spectroscopic instrument comprises a projecting optical system for projecting a projecting light emitted from a light source, a photodetecting optical system for receiving a reflection light from an object to be measured and for guiding to a photodetection member, and a spectroscope for detecting a condition of the object to be measured based on the reflection light as received by the photodetection member, wherein the projecting optical system and the photodetecting optical system have a projecting system chromatic aberration decreasing component and a photodetecting system chromatic aberration decreasing component which eliminate chromatic aberrations, respectively. As a result, the chromatic aberration is corrected and the measurement accuracy can be improved, a working time can be shortened without the need to perform an additional processing for the correction of the chromatic aberration, and a working efficiency can be improved.

DETAILED DESCRIPTION OF THE PREFERRED EMBODIMENT

A description will be given below on embodiments of the present invention by referring to the attached drawings.

First, referring to FIG. 1, a description will be given on a first embodiment.

Figure 1:
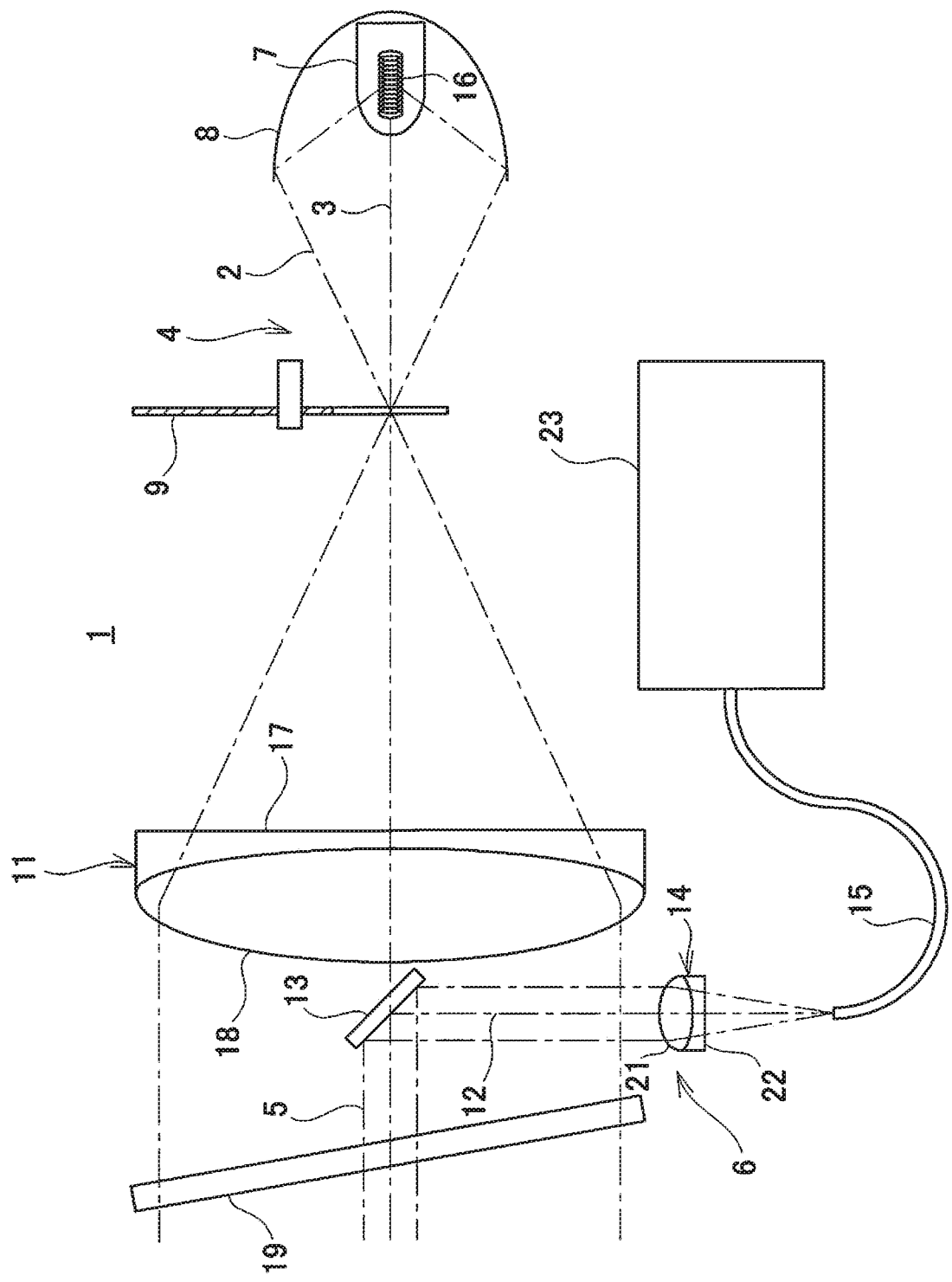
FIG. 1 shows a block diagram of an optical system of a spectroscopic instrument according to a first embodiment.

In FIG. 1, reference numeral 1 denotes a spectroscopic instrument. The spectroscopic instrument 1 has a projecting optical system 4 for projecting a projecting light 2 including a near-infrared light on a projecting optical axis 3, and a photodetecting optical system 6 for receiving a reflection light 5 from an object to be measured (not shown).

The projecting optical system 4 has the projecting optical axis 3, and an elliptical mirror 8, an optical chopper 9 and a projecting system lens group 11, which is a projecting system chromatic aberration decreasing component, are provided on the projecting optical axis 3. Further, a light source 7 is provided on the projecting optical axis 3 and configured so that a light from the light source 7 is projected to the object to be measured by the projecting optical system 4.

Further, the photodetecting optical system 6 has a photodetecting optical axis 12, and a mirror 13 and a photodetecting system lens group 14, which is a photodetecting system chromatic aberration decreasing component, are provided on the photodetecting optical axis 12. Further, at a focal position of the photodetecting system lens group 14, a photodetection fiber 15, which is a photodetection member, is provided. The photodetecting optical axis 12 crosses the projecting optical axis 3, and the mirror 13 is disposed on this crossing position. The mirror 13 is provided in such manner that at least one part of the reflection light 5 is reflected on the photodetecting optical axis 12.

The light source 7 is, for instance, a halogen lamp which emits the projecting light 2 including a near-infrared light. By impressing an electric current to a filament 16, the projecting light 2 including the near-infrared light in a wavelength range of about 0.8 µm to 2.5 µm, for instance, is emitted. It is to be noted that a halogen heater may be used instead of the halogen lamp. The halogen heater is to heat by radiant heat emitted from the filament 16. Due to radiation of radiant heat from the filament 16, since the light including the near-infrared light is emitted, the light as emitted can be used as the light source.

The elliptical mirror 8 is disposed in such a manner that the elliptical mirror 8 surrounds the light source 7. The elliptical mirror 8 reflects the projecting light 2 as emitted from the light source 7 and converged to the optical chopper 9 on the projecting optical axis 3. The optical chopper 9 performs chopping of the projecting light 2 at a predetermined frequency. When the projecting light 2 passes through the optical chopper 9, the projecting light 2 of a specified frequency is projected intermittently to the object to be measured.

The position where the optical chopper 9 is provided is a focusing position of the projecting light 2 as reflected by the elliptical mirror 8, i.e. the position of a secondary light source when the light source 7 is regarded as a primary light source. Here, the light source 7 is a halogen lamp, and since the projecting light 2 is emitted from the spectroscopic filament 16, the projecting light 2 as reflected by the elliptical mirror 8 is not focused to a point. Therefore, at the secondary light source position, the projecting light 2 will be a blurred point image with a luminous flux diameter of about 10 mm.

The projecting system lens group 11 comprises a projecting system concave lens 17 and a projecting system convex lens 18, and a position is set up in such manner that a focal position of the projecting system lens group 11 becomes an approximate secondary light source position, i.e. so as to become the focusing position of the projecting light 2 by the approximate elliptical mirror 8. Due to the fact that the projecting system concave lens 17 and the projecting system convex lens 18 are combined to constitute the projecting system lens group 11, a chromatic aberration to occur in the optical system of the spectroscopic instrument 1 is corrected.

As to be the projecting system concave lens 17 and the projecting system convex lens 18, high NA lens with a longer focal length is used and the projecting system lens group 11 is set so that the focal length of the projecting system lens group 11 will be 2 meters to 10 meters, for instance.

After passing through the optical chopper 9, the projecting light 2 enters the projecting system lens group 11. The projecting light 2 is set as approximate parallel luminous fluxes, and is projected to the object to be measured after passing through a window member 19. It is to be noted that it is desirable that the window member 19 is made of a material, which has a high transmissivity with respect to the near-infrared light with a wavelength to the same degree as the near-infrared light included in the projecting light 2 as emitted from the light source 7, i.e. the near-infrared light of about 0.8 µm to 2.5 µm.

The mirror 13 is arranged so as to reflect at least one part of the reflection light 5 from the object to be measured on the photodetecting optical axis 12. Further, it is so arranged that the reflection light 5 as reflected by the mirror 13 enters the photodetecting system lens group 14.

The photodetecting system lens group 14 comprises a photodetecting system convex lens 21 and a photodetecting system concave lens 22, and a chromatic aberration occurring in the optical system of the spectroscopic instrument 1 is corrected.

As the photodetecting system convex lens 21 and the photodetecting system concave lens 22, a lens with NA as small in size as the optical fiber and with a shorter focal length, is used. After being converged by the photodetecting system lens group 14, the reflection light 5 enters a light receiving end surface of the photodetection fiber 15.

The photodetection fiber 15 is an optical fiber, for instance, and a fiber diameter is 0.6 mm or smaller. After being received by the photodetection fiber 15, the reflection light 5 is inputted to a spectroscope 23 via the photodetection fiber 15. The spectroscope 23 performs a spectroscopic analysis on the reflection light 5, which is inputted via the photodetection fiber 15. More concretely, a spectral information obtained from the reflection light 5 is compared with a spectral information of the near-infrared light with respect to a reference sample as measured in advance, and an information relating to the condition of the object to be measured, e.g. material or composition, is obtained.

As the spectroscope 23, a system where the reflection light 5 is spectroscopically analyzed by a diffraction grating, a prism, an LVF (Linear Variable Filter), or a system where a plurality of wavelength range obtained by an optical filter, and the like, is available. Further, as a light detecting element to be used in the spectroscope 23, various types of detecting elements such as an APD (Avalanche Photodiode), a line sensor, and the like, is available.

Further, in the spectroscopic instrument 1, the photodetecting system lens group 14 is designed as smaller with respect to the projecting system lens group 11. This is based on the reason that it is better if the NA of the photodetecting system lens group 14 is smaller in order to maintain the wavelength resolving power of the spectroscope 23, that if the focal distance of the photodetecting system lens group 14 is made longer, the spectroscopic instrument 1 itself becomes larger size, and that when the NA of the photodetecting system lens group 14 is constant, photodetection amount does not change almost at all even if the lens diameter is increased. Further, since the size of the mirror 13 corresponds to the diameter of the photodetecting system lens group 14, the mirror 13 can be made in smaller size when the photodetecting system lens group 14 is made in smaller size.

Next, a description will be given on an operation of the spectroscopic instrument 1.

When electric current is impressed to the filament 16, the projecting light 2 is emitted from the light source 7. The projecting light 2 is reflected by the elliptical mirror 8 and converted to a secondary light source position, where the optical chopper 9 is provided.

The projecting light 2 is chopped during the process of passing through the optical chopper 9, and an external disturbance light is eliminated and becomes the projecting light 2 having an intermittent specified frequency. The projecting light 2 enters the projecting system lens group 11, set as approximate parallel luminous fluxes in the projecting system lens group 11, and is projected to the object to be measured by passing through the window member 19.

The reflection light 5 as reflected by the object to be measured passes through the window member 19 and enters the mirror 13. The reflection light 5 is reflected by the mirror 13 and is deflected along the photodetecting optical axis 12. Further, the reflection light 5 is converged by the photodetecting system lens group 14 and is received by the photodetection fiber 15.

The reflection light 5, as received by the photodetection fiber 15, is guided to the spectroscope 23. In the spectroscope 23, spectroscopic analysis of the reflection light 5 is performed, and composition and material of the object to be measured are analyzed. For instance, when salinity concentration in the concrete changes, a spectral information of the reflection light 5 changes. Therefore, a salinity concentration in the concrete is measured based on the spectral information of the reference sample as measured in advance and the spectral information of the reflection light 5, and the degree of deterioration of the concrete can be judged based on the measurement result.

As described above, in the spectroscopic instrument 1 of the present embodiment, the projecting system concave lens 17 and the projecting system convex lens 18 are combined as the projecting system lens group 11, and the photodetecting system convex lens 21 and the photodetecting system concave lens 22 are combined as the photodetecting system lens group 14. Therefore, chromatic aberration is corrected by the projecting system lens group 11 and the photodetecting system lens group 14, and a highly accurate spectroscopic measurement can be carried out.

Further, in the spectroscopic instrument 1, chromatic aberration can be corrected by the projecting system lens group 11 and the photodetecting system lens group 14. Therefore, there is no need to perform measurement of spectral reflectivity of the reference diffusing reflecting object and distance measurement in advance and correct the influence of chromatic aberration by comparing the measurement result with result of the measurement in advance. As a result, working time is shortened and working efficiency can be improved.

Further, in the first embodiment, the spectroscopic instrument 1 is adapted to measure the condition of the object to be measured by performing spectroscopic analysis on the reflection light 5 from the object to be measured. That is, it is possible to measure the object to be measured at a distant position on a non-contact basis. Therefore, when measurement is performed on large size structures such as tunnels or bridges or the like, there is no need to put up a scaffolding, and this contributes to the improvement of working efficiency.

Further, in the spectroscopic instrument 1, chromatic aberration is corrected by the projecting system lens group 11 and the photodetecting system lens group 14. Therefore, even in a case where there is wavelength difference in diffusing reflecting characteristics of the object to be measured, it is possible to decrease the influence of the wavelength difference.

Further, by disposing the mirror 13 at the crossing position of the projecting optical axis 3 and the photodetecting optical axis 12, the optical system can be simplified and miniaturized.

The mirror 13 is designed as smaller than the projecting system lens group 11. Therefore, even in a case where the projecting light 2, which has been set as approximate parallel luminous fluxes in the projecting system lens group 11 is blocked by the mirror 13, the projecting light 2 in sufficient light amount can be projected and the reflection light 5 in sufficient light amount can be obtained for spectroscopic measurement.

Further, since the filament 16 is a light source having an area, the projecting light 2 as projected from the filament 16 and reflected by the elliptical mirror 8 becomes a blurred point image at the secondary light source position with a luminous flux diameter of about 10 mm. That is, since the projecting light 2 is not concentrated to a point, a secondary light source of approximately the same level can be obtained even when the optical chopper 9 is moved to some extent. Therefore, it is not necessary to perform strict positioning between the focal position of the projecting system lens group 11 and the secondary light source position, and this contributes to the improvement of working efficiency.

Further, the projecting light 2 reflected on the elliptical mirror 8 is not concentrated to a point. That is, since the projecting light 2 from the secondary light source includes a light which can not be set as parallel luminous fluxes by the projecting system lens group 11, the photodetecting optical system 6 may receive the reflection light 5 of a portion which is blocked by the mirror 13 in case luminous fluxes is parallel. Therefore, a more sufficient light amount of the reflection light 5 can be obtained, and it becomes possible to perform spectroscopic measurement within an extremely near distance.

Figure 2:
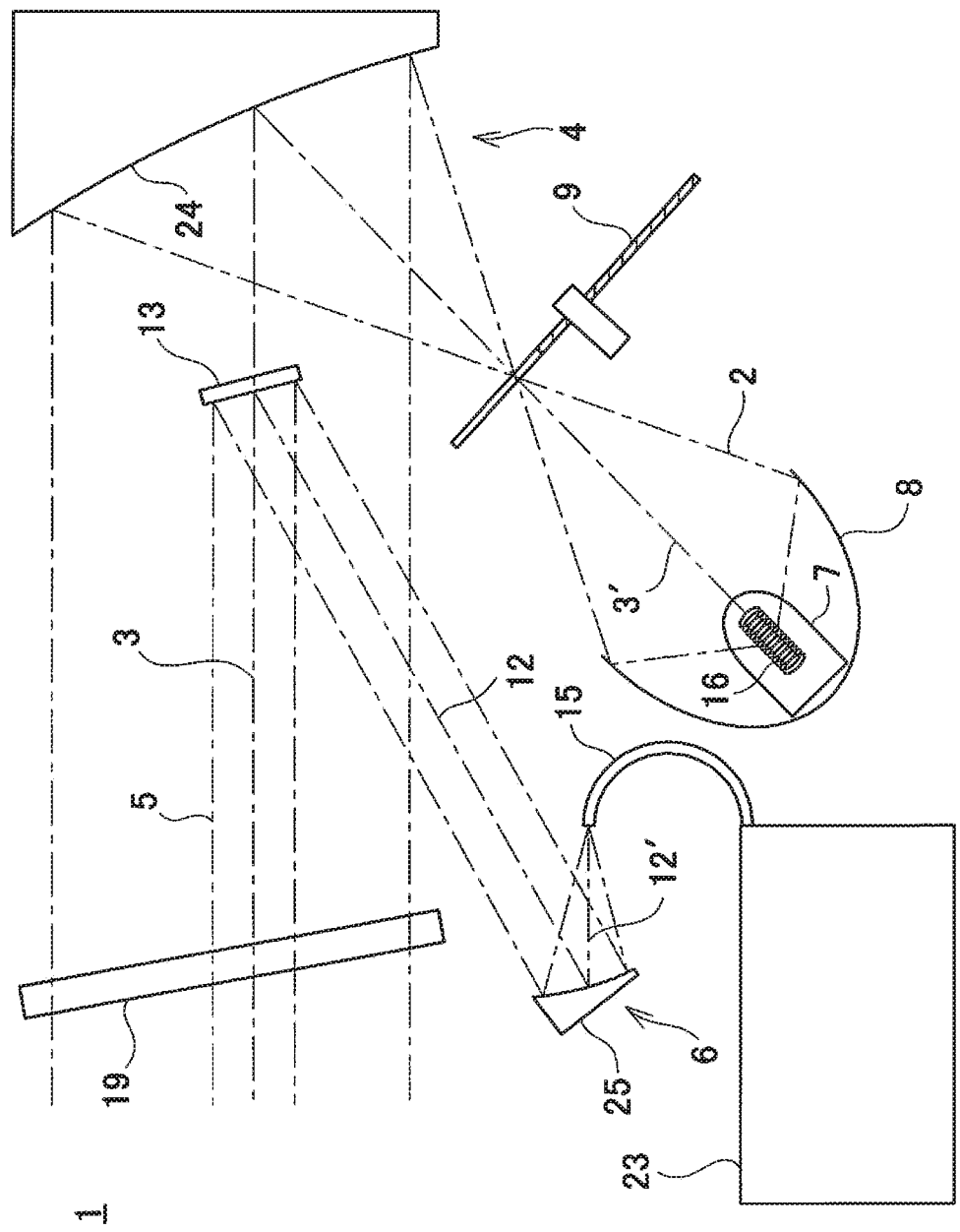
FIG. 2 shows a block diagram of an optical system of a spectroscopic instrument according to a second embodiment.

Next, referring to FIG. 2, a description will be given on a second embodiment. It is to be noted that in FIG. 2, what are equivalent to components in FIG. 1 are referred by the same symbol, and detailed description is not given here.

In the spectroscopic instrument 1 of the second embodiment, instead of the projecting system lens group 11 (see FIG. 1) and the photodetecting system lens group 14 (see FIG. 1) in the first embodiment, a projecting system reflection mirror 24 which is a projecting system chromatic aberration decreasing component and a photodetecting system reflection mirror 25 which is a photodetecting system chromatic aberration decreasing component, are provided.

The projecting system reflection mirror 24 has a reflection surface which is a free form surface or an off-axis paraboloid surface and deflects a projecting optical axis 3' to a projecting optical axis 3 and reflects the projecting light 2 from the optical chopper 9 as provided at a secondary light source position to be set as the approximate parallel luminous fluxes. It is to be noted that similarly to the projecting system lens group 11, the projecting system reflection mirror 24 has a much larger diameter than the mirror 13. The projecting system reflection mirror 24 is provided in such a manner that a focal position of the projecting system reflection mirror 24 is approximately at the position of the second light source.

Further, the photodetecting system reflection mirror 25 has a reflection surface which is a free form surface or an off-axis paraboloid surface. Further, the photodetecting system reflection mirror 25 deflects a photodetecting optical axis 12 to a photodetecting optical axis 12' and reflects the reflection light 5, which is an approximate parallel luminous flux, so as to be converged to a light receiving end surface of a photodetection fiber 15.

The projecting light 2 as emitted from a light source 7 is reflected by an elliptical mirror 8 and passes through the optical chopper 9 which is provided on the secondary light source position. The projecting light 2 is chopped during the process of passing through the optical chopper 9, an external disturbance light is eliminated, and becomes the projecting light 2 having an intermittent specified frequency. The projecting light 2 is reflected so as to be set as approximate parallel luminous fluxes by the projecting system reflection mirror 24 and is projected to the object to be measured by passing through the window member 19.

The reflection light 5 as reflected by the object to be measured passes through the window member 19 and enters the mirror 13. The reflection light 5 as reflected by the mirror 13 is further reflected by the photodetecting system reflection mirror 25, converged to a light receiving end surface of the photodetection fiber 15, and received.

The reflection light 5 as received by the photodetection fiber 15 is guided to a spectroscope 23 and by being subjected to a spectroscopic analysis, composition and material, etc. of the object to be measured are analyzed.

In the second embodiment, the spectroscopic instrument 1 is an optical system, which uses the projecting system reflection mirror 24 and the photodetecting system reflection mirror 25 and lens is not used. Therefore, a chromatic aberration does not occur and it is possible to perform a highly accurate spectroscopic measurement.

Because the spectroscopic instrument 1 does not need an optical system or processing for correcting chromatic aberration, an instrument structure is simplified, working time is shortened and the working efficiency can be improved.

Further, the projecting system reflection mirror 24 and the photodetecting system reflection mirror 25 are optical systems in which no chromatic aberration occurs. Therefore, even in a case where there is wavelength difference in diffusing reflecting characteristics of the object to be measured, it is possible to decrease the influence of the wavelength difference.

Further, in the second embodiment, since the projecting system reflection mirror 24 and the photodetecting system reflection mirror 25 are used and lens are not used, the optical system can be miniaturized, and this makes it possible to miniaturize the spectroscopic instrument 1.

It is to be noted that in the first embodiment and the second embodiment, an angle detector, a range finder, a laser pointer, etc. may be further provided on the spectroscopic instrument 1. By providing the angle detector or the range finder, it is possible to specify the measuring position in an easy manner even when the object to be measured is separated at a distance. Further, by providing the laser pointer, in a case where the measurement is performed during day time and outdoors, or in a case where it is difficult to visually confirm the projecting light 2 as projected, the measuring position can be visually confirmed in an easier manner.

Further, in the first embodiment and the second embodiment, description has been given on a case where the degree of deterioration of the concrete is judged by the spectroscopic instrument 1, but the object to be measured is not limited to the concrete, and other material can be used as the object to be measured as long as its spectral information changes depending on conditions such as wood, plant, food, ceramics, metal or various types of building materials and the like.

Further, the light source 7 is not limited to a halogen lamp or a halogen heater which has the filament 16, and any other material may be used as long as a light-emitting area is large so that the light is not converged to a point when reflected by the elliptical mirror 8.

Further, frequency of the light to be used for the spectroscopic measurement is not limited to the range of 0.8 μm to 2.5 μm, and it can be set adequately, depending on the purpose of use.

The invention claimed is:

1. A spectroscopic instrument comprising: a projecting optical system for projecting a projecting light emitted from a light source toward an object to be measured, a photodetecting optical system for receiving a reflection light from said object to be measured and for guiding to a photodetection member, and a spectroscope for detecting a condition of said object to be measured based on said reflection light as received by said photodetection member, wherein said projecting optical system comprises a projecting system chromatic aberration decreasing component disposed between the light source and the object to be measured and said photodetecting optical system comprises a photodetecting system chromatic aberration decreasing component disposed between the object to be measured and the photodetection member, wherein the projecting system chromatic aberration decreasing component and the photodetecting system chromatic aberration decreasing component eliminate chromatic aberrations.

2. The spectroscopic instrument according to claim 1, wherein said photodetecting optical system has a mirror for reflecting one part of said reflection light from said object to be measured, wherein said projecting optical system and said photodetecting optical system are disposed in such a manner that a projecting optical axis and a photodetecting optical axis cross each other, and said mirror is provided at a crossing position of said projecting optical axis and said photodetecting optical axis.

3. The spectroscopic instrument according to claim 2, wherein a diameter of said projecting system chromatic aberration decreasing component is larger than a diameter of said mirror.

4. The spectroscopic instrument according to claim 3, wherein said projecting system chromatic aberration decreasing component is a projecting system lens group having a projecting system concave lens and a projecting system convex lens, and said photodetecting system chromatic aberration decreasing component is a photodetecting system lens group having a photodetecting system concave lens and a photodetecting system convex lens.

5. The spectroscopic instrument according to claim 3, wherein said projecting system chromatic aberration decreasing component is a projecting system reflection mirror having a reflection surface of a free form surface or an off-axis paraboloid surface, and said photodetecting system chromatic aberration decreasing component is a photodetecting system reflection mirror having a reflection surface of a free form surface or an off-axis paraboloid surface.

6. The spectroscopic instrument according to claim 3, wherein said light source is a filament for emitting said projecting light including a near-infrared light, wherein said projecting optical system has an elliptical mirror, and said projecting system chromatic aberration decreasing component is disposed so that a focusing position of said projecting light reflected by said elliptical mirror approximately coincides with a focal position of said projecting system chromatic aberration decreasing component.

7. The spectroscopic instrument according to claim 2, wherein said projecting system chromatic aberration decreasing component is a projecting system lens group having a projecting system concave lens and a projecting system convex lens, and said photodetecting system chromatic aberration decreasing component is a photodetecting system lens group having a photodetecting system concave lens and a photodetecting system convex lens.

8. The spectroscopic instrument according to claim 2, wherein said light source is a filament for emitting said projecting light including a near-infrared light, wherein said projecting optical system has an elliptical mirror, and said projecting system chromatic aberration decreasing component is disposed so that a focusing position of said projecting light reflected by said elliptical mirror approximately coincides with a focal position of said projecting system chromatic aberration decreasing component.

9. The spectroscopic instrument according to claim 2, wherein said projecting system chromatic aberration decreasing component is a projecting system reflection mirror having a reflection surface of a free form surface or an off-axis paraboloid surface, and said photodetecting system chromatic aberration decreasing component is a photodetecting system reflection mirror having a reflection surface of a free form surface or an off-axis paraboloid surface.

10. The spectroscopic instrument according to claim 1, wherein said projecting system chromatic aberration decreasing component is a projecting system lens group having a projecting system concave lens and a projecting system convex lens, and said photodetecting system chromatic aberration decreasing component is a photodetecting system lens group having a photodetecting system concave lens and a photodetecting system convex lens.

11. The spectroscopic instrument according to claim 1, wherein said projecting system chromatic aberration decreasing component is a projecting system reflection mirror having a reflection surface of a free form surface or an off-axis paraboloid surface, and said photodetecting system chromatic aberration decreasing component is a photodetecting system reflection mirror having a reflection surface of a free form surface or an off-axis paraboloid surface.

12. The spectroscopic instrument according to claim 1, wherein said light source is a filament for emitting said projecting light including a near-infrared light, wherein said projecting optical system has an elliptical mirror, and said projecting system chromatic aberration decreasing component is disposed so that a focusing position of said projecting light reflected by said elliptical mirror approximately coincides with a focal position of said projecting system chromatic aberration decreasing component.

\* \* \* \* \*